United States Patent
Lin et al.

(10) Patent No.: US 11,497,440 B2
(45) Date of Patent: Nov. 15, 2022

(54) HUMAN-COMPUTER INTERACTIVE REHABILITATION SYSTEM

(71) Applicant: Fu Jen Catholic University, New Taipei (TW)

(72) Inventors: Chien-Wen Lin, New Taipei (TW); Chia-Hsiang Lee, New Taipei (TW); Yu-Jen Chen, New Taipei (TW); Jui-Yun Hung, New Taipei (TW)

(73) Assignee: FU JEN CATHOLIC UNIVERSITY, New Taipei (TW)

( * ) Notice: Subject to any disclaimer, the term of this patent is extended or adjusted under 35 U.S.C. 154(b) by 495 days.

(21) Appl. No.: 16/655,308

(22) Filed: Oct. 17, 2019

(65) Prior Publication Data
US 2020/0121247 A1  Apr. 23, 2020

Related U.S. Application Data

(60) Provisional application No. 62/746,586, filed on Oct. 17, 2018.

(51) Int. Cl.
| | |
|---|---|
| A61B 5/00 | (2006.01) |
| H04W 76/10 | (2018.01) |
| H04L 67/10 | (2022.01) |
| A61B 5/11 | (2006.01) |
| A61B 3/024 | (2006.01) |
| A61B 5/389 | (2021.01) |
| H04L 65/402 | (2022.01) |
| A61H 5/00 | (2006.01) |
| G06F 3/14 | (2006.01) |
| A63B 23/16 | (2006.01) |

(52) U.S. Cl.
CPC .............. *A61B 5/486* (2013.01); *A61B 3/024* (2013.01); *A61B 5/0022* (2013.01); *A61B 5/1125* (2013.01); *A61B 5/389* (2021.01); *A61B 5/742* (2013.01); *H04L 65/4025* (2022.05); *H04L 67/10* (2013.01); *H04W 76/10* (2018.02); *A61B 2505/09* (2013.01); *A61H 5/00* (2013.01); *A63B 23/16* (2013.01); *G06F 3/14* (2013.01)

(58) Field of Classification Search
CPC ........................... A61B 2505/09; A61B 3/024
USPC ....................................................... 600/301
See application file for complete search history.

(56) References Cited

U.S. PATENT DOCUMENTS

| | | | | |
|---|---|---|---|---|
| 9,311,789 B1 * | 4/2016 | Gwin | ..................... | G08C 19/00 |
| 2005/0216243 A1 * | 9/2005 | Graham | ................. | G16H 40/67 |
| | | | | 703/11 |

(Continued)

*Primary Examiner* — Fabricio R Murillo Garcia
(74) *Attorney, Agent, or Firm* — WPAT, PC

(57) ABSTRACT

The present invention provides a human-computer interactive rehabilitation system, which can automatically calculate rehabilitation strength suitable for the patient, so that it is not necessary to manually evaluate and adjust the parameter settings in human-computer interactive rehabilitation system when different patients use it. At the same time, the human-machine interactive rehabilitation system and the hospital end can track the rehabilitation status and intervene through the data platform at any time. The platform establishes a cloud community feedback and encouragement mechanism, and immediately transmits the rehabilitation results to the designated barriers of the patients, provides patient encouragement feedback, and strengthens the community interaction and linkage in the medical relationship.

6 Claims, 18 Drawing Sheets

(56) References Cited

U.S. PATENT DOCUMENTS

| | | | |
|---|---|---|---|
| 2011/0144018 A1* | 6/2011 | Matayoshi | A61P 25/04 514/11.9 |
| 2012/0029391 A1* | 2/2012 | Sung | A61B 5/6824 600/595 |
| 2017/0340502 A1* | 11/2017 | Roh | A63B 21/4035 |

* cited by examiner

- Take the farm milking as an example in the design of this interactive content ~40
- The main rehabilitation action setting is the training of the hand extension and grip of the patient ~41
- Every time the patient makes a grip with enough strength, it is considered to have once squeezed milk ~42
- When squeezed milk to 40 times, it is considered to be a bucket of milk. If the amount of rehabilitation needs to squeeze 3 barrels of milk a day, the patient must complete 120 times of rehabilitation action with hand extension and grip every day ~43
- In the visual design of interactive content, in order to increase the sense of fun and reality, the scenes around the scene are used, so that the patient can use the left and right turns to surround the farm scene while rehabilitating ~44
- At the same time, in order to prevent the patient from returning to the original milking scene while watching, the interactive program automatically returns the screen to the main milking scene position when it detects that the patient's head is not rotating ~45
- In addition, in the action feedback of milking, the milky white area of the cow will decrease, and the milky white area in the lower bucket will also rise; and every time the patient squeeze it, the farmer's hand in the picture will follow the action of squeezing it; to increase the link with the movement of the rehabilitation ~46
- The use of non-fully immersed intelligent augmented reality glasses on the visual device allows the patient to see the surrounding environment in addition to the interactive content during the interactive rehabilitation, reducing the overall dizziness and fear caused by fully immersive viewing ~47

FIG. 3

HUMAN-COMPUTER INTERACTIVE REHABILITATION SYSTEM

CROSS-REFERENCE TO RELATED APPLICATION

This application claims priority of U.S. provisional application No. 62/746,586, filed on Oct. 17, 2018, the content of which are incorporated herein in its entirety by reference.

BACKGROUND OF THE INVENTION

1. Field of the Invention

The present invention relates to a human-computer interactive rehabilitation system, and particularly to a human-computer interactive rehabilitation system for patients with stroke sequelae, and more particularly to a human-computer interactive rehabilitation system which is complemented by games and animations to achieve dynamic challenges to simulate the rehabilitation system of the actual environmental conditions faced by patients with stroke sequelae.

2. The Prior Art

In Taiwan, about 17,000 people lose their daily lives because of a stroke. Stroke is the number one cause of adult disabilities. Wherein, the studies showed that the six months after the onset of stroke was the golden period of rehabilitation, and the recovery of exercise capacity was the fastest, especially in the first three months. About 40% of stroke patients receiving rehabilitation therapy have a good recovery in upper limb function and about 90% of people can walk on their own. This result shows that the care and rehabilitation treatment plan for patients with stroke after discharge is of great help to self-care ability of patients and family care.

However, even if the brain injury patient goes to the rehabilitation clinic, it is not enough to carry out a 30-minute to one-hour rehabilitation. In addition, the common sequelae of stroke include impaired motor function, impaired language function, and the spatial neglect syndrome, which greatly affects the patient's ability to take care of themselves and even poses a personal safety risk. However, according to medical unit surveys, the form of rehabilitation for the spatial neglect syndrome is mostly static, but the real challenges faced by patients in the real environment are mostly dynamic. For example, on the left side, traditional rehabilitation can hardly train enough ability to adapt to life, and the rehabilitation content is boring, the action is single and repeated, the effect is not good enough to ignite the rehabilitation motivation of patients.

With the development of technology, as well as the popularity of smart phones and augmented reality, it is expected to develop a game and animation in a dynamic form, and to achieve dynamic challenges, try to simulate the environmental conditions that patients actually face. At the same time, through the concept of game prescription, the fun and practicality of rehabilitation is added, in order to overcome the space and time constraints, improve the quality of rehabilitation and intensity, to effectively improve the effect of rehabilitation, and help patients to regain their self-care as soon as possible. The invention is really necessary for the rehabilitation system, combined with the rehabilitation game to assist the hospital, so that the patient can also rebuild at home, in order to reduce the current consumption of health care resources.

SUMMARY OF THE INVENTION

To solve the foregoing problem, one objective of the present invention is to provide a rehabilitation system for a patient with stroke sequelae, including: a visual device for providing a guide screen to a patient; a limb sensor which is worn on a limb of the patient to sense a motion of the limb to generate a sensing signal; and an information processing unit which establishes wireless communication with the visual device and the limb sensor, and the information processing unit comprises an input signal processing module, a rehabilitation operation weight processing module, and a content feedback presentation module; wherein, the content feedback presentation module transmits the guidance screen to the visual device, and the input signal processing module receives the sensing signal from the limb sensor and transmits the sensing signal to the rehabilitation operation weight processing module, and then the rehabilitation operation weight processing module estimates the current hand motion of the patient according to the sensing signal, and derives various actions of the patient to determine a recovery degree of stroke sequelae of the patient's limb, and the rehabilitation operation weight processing module simultaneously parameterizes the sensing signal into a range of values as the patient's current force state, and automatically adjusts a maximum of the range applicable to the patient to calculate a rehabilitation strength suitable for the patient based on the patient's current force state, and the content feedback presentation module changes a content of the guide screen to demonstrate the rehabilitation strength suitable for the patient; wherein, the content feedback presentation module uploads the recovery degree of stroke sequelae of the patient to a cloud server.

In one embodiment of the present invention, the stroke sequelae is about a hand movement disorder and the limb sensor is a muscle current sensor; the guide screen is to direct the patient to perform a hand grip training; the guiding screen guides the patient to perform the hand grip training according to the sensing signal and the rehabilitation strength suitable for the patient; and the recovery degree of stroke sequelae of the patient is related to autonomous movement and arm muscle control.

Another objective of the present invention is to provide a rehabilitation system for a patient with stroke sequelae, comprising: a visual device for providing a guide screen to a patient; and an information processing unit which comprises a human machine interface and establishes wireless communication with the visual device, and the information processing unit further comprises an input signal processing module, a rehabilitation operation weight processing module, and a content feedback presentation module; wherein, the content feedback presentation module transmits the guidance screen to the visual device, and the human machine interface receives an input data inputted by the patient, and provides the input data to the rehabilitation operation weight processing module to determine a recovery degree of stroke sequelae of the patient, and the rehabilitation operation weight processing module automatically parameterizes the input data into a rehabilitation strength suitable for the patient, and the content feedback presentation module changes a content of the guide screen to demonstrate the rehabilitation strength suitable for the patient; wherein, the content feedback presentation module uploads the recovery degree of stroke sequelae of the patient to a cloud server.

In one embodiment of the present invention, the stroke sequelae is about a visual disorder; the guide screen is to direct the patient count a plurality of objects, and the patient's count number; the recovery degree of stroke sequelae of the patient relates to a field vision of the patient; and the rehabilitation strength is a size of the field vision of the guidance screen which is seen by the patient.

The human-computer interactive rehabilitation system of the present invention can automatically adjust to different patients according to the maximum output range of different patients in the practice of the hand extension and grip rehabilitation of patients with stroke sequelae; and in the rehabilitation practice of the patient with stroke sequelae of the visual disorder, the field vision of patients can be automatically determined by the data input by the patient to infer the affected side of the specific spatial field of view of different patients, and the input signal processing module automatically estimates a rehabilitation strength suitable for the patient. In this way, when using the human-computer interactive rehabilitation system of the present invention, different patients do not need to manually evaluate and adjust the parameter settings in the system in advance, that is, when the sensing signals or the input data are quantized, the numerical normalization processing is performed in advance. The human-computer interactive rehabilitation system of the present invention designs different levels of interactive content according to different operation difficulty levels, and different levels of interactive content are different in operation setting, thereby improving rehabilitation efficiency after stroke.

The human-computer interactive rehabilitation system of the present invention can track the rehabilitation status and intervene at any time through the data platform, establish a cloud community feedback encouragement mechanism on the platform, and immediately transmit the rehabilitation result to the patient designated caretaker, and then, to provide patient encouragement feedback and strengthen community interaction and link in medical relationship. The human-computer interactive rehabilitation system of the present invention also stores the operation value of each time, so that in addition to being able to automatically adjust the rehabilitation content suitable for different patients immediately, the physician can also give a new prescription from the remote end through the cloud server. In addition, if the patient cannot immediately reach the rehabilitation strength of the new prescription, the human-computer interactive rehabilitation system of the present invention automatically adjusts the current rehabilitation strength suitable for the patient as described above, and the human-computer interactive rehabilitation system of the present invention will gradually strengthen the rehabilitation strength based on the new prescriptions from the doctors, so that the patient can continue to rebuild the confidence without giving up because of the inability to complete the reconstruction strength.

Therefore, the human-computer interactive rehabilitation system of the present invention can be used for the reconstruction of stroke sequelae, and can enter the home reconstruction through legal retailing and provide qualified people, families, or unit rents. The human-computer interactive rehabilitation system of the present invention can also be used in conjunction with local rehabilitation hospitals and clinics in conjunction with relevant acute post-care policies and comprehensive elderly care plans, and is applied to rehabilitation hospitals for rehabilitation prescription and treatment, and can also cooperate with community rehabilitation, home health care and technical care to provide patients in need.

The embodiments of the present invention are further described with the following drawings. The following embodiments are given to illustrate the present invention and are not intended to limit the scope of the present invention, and those having ordinary skill in the art can make some modifications and refinements without departing from the spirit and scope of the present invention. Therefore, the scope of the present invention is defined by the scope of the appended claims.

BRIEF DESCRIPTION OF THE DRAWINGS

FIG. 3 shows the flow chat of the farm milking game in the human-computer interactive rehabilitation system of one embodiment of the present invention.

DETAILED DESCRIPTION OF THE PREFERRED EMBODIMENT

Figure 1:
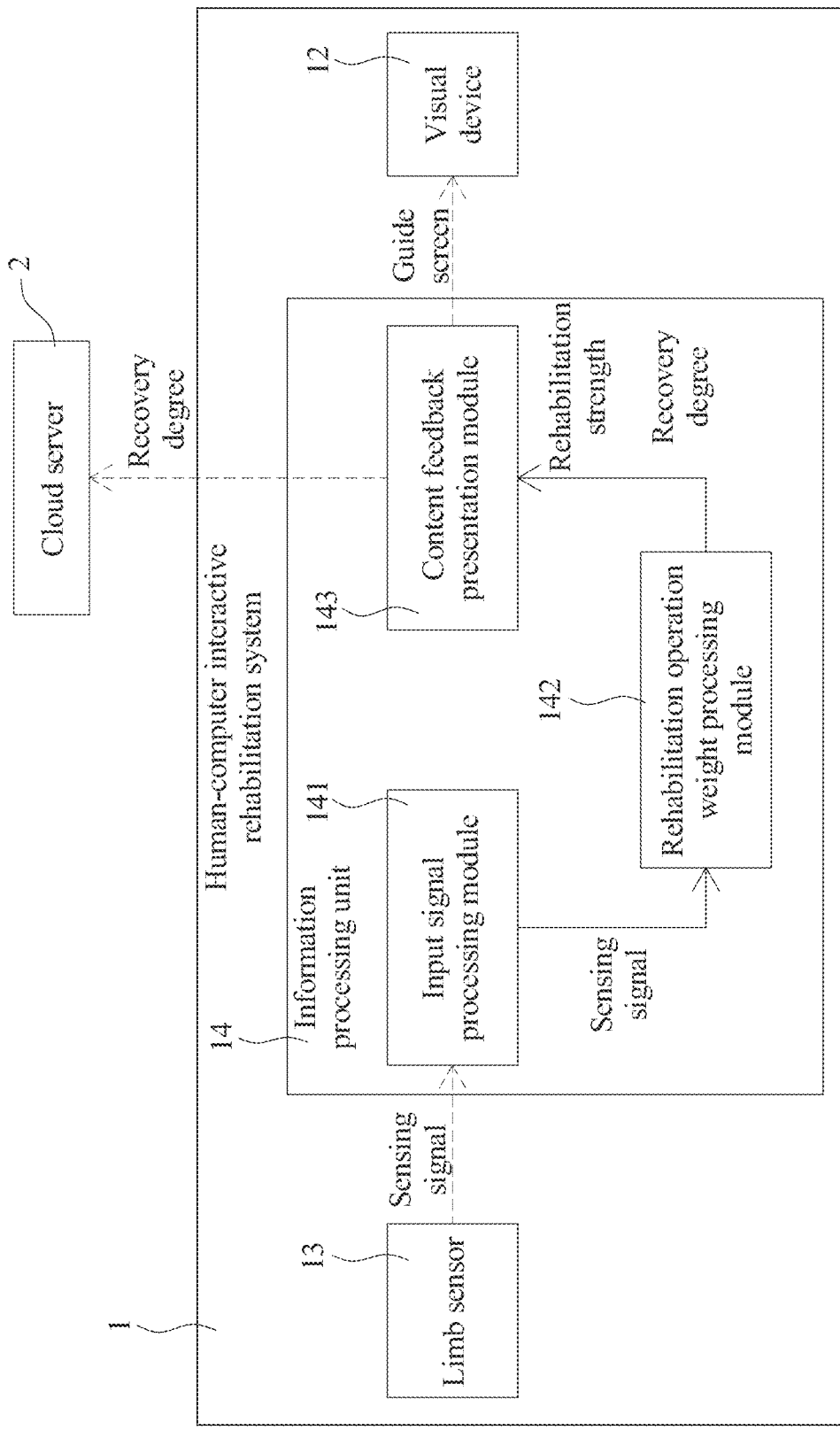
FIG. 1 shows the architecture diagram of the human-computer interactive rehabilitation system of the present invention for the rehabilitation of the hand extension and grip.

According to the present invention, the operating procedures and parameter conditions for limb sensor are within the professional literacy and routine techniques of those having ordinary skill in the art.

According to the present invention, the operating procedures and parameter conditions for visual device are within the professional literacy and routine techniques of those having ordinary skill in the art.

The present invention provides a human-machine interactive rehabilitation system 1 capable of automatically estimating a rehabilitation strength suitable for a patient based on information obtained from the patient in the rehabilitation of hand extension and grip of patients with stroke sequelae, and the rehabilitation of patients with stroke sequelae of visual disorder. In this way, when using the human-computer interactive rehabilitation system 1 of the present invention, different patients do not need to manually evaluate and adjust the parameter settings in the system in advance, that is, when the sensing signals or the input data are quantized, the numerical normalization processing is performed in advance. The human-computer interactive rehabilitation system 1 of the present invention designs different levels of interactive content according to different operation difficulty levels, and different levels of interactive content are different in operation setting, thereby improving rehabilitation efficiency after stroke.

Meanwhile, the human-computer interactive rehabilitation system 1 of the present invention is connected with the cloud server 2 at the hospital end and can track the rehabilitation status and intervene at any time through the data platform, establish a cloud community feedback encouragement mechanism on the platform, and immediately transmit the rehabilitation result to the patient designated caretaker, and then, to provide patient encouragement feedback and strengthen community interaction and link in medical relationship.

Therefore, the human-computer interactive rehabilitation system of the present invention can be used for the reconstruction of stroke sequelae, and can enter the home reconstruction through legal retailing and provide qualified people, families, or unit rents. The human-computer interactive rehabilitation system of the present invention can also be used in conjunction with local rehabilitation hospitals and clinics in conjunction with relevant acute post-care policies and comprehensive elderly care plans, and is applied to rehabilitation hospitals for rehabilitation prescription and treatment, and can also cooperate with community rehabilitation, home health care and technical care to provide patients in need.

The exercise of the hand extension and grip rehabilitation of the patient with stroke sequelae and the rehabilitation of the patient with stroke sequelae of visual disorder by the human-computer interactive rehabilitation system 1 of the present invention will be described in detail below. In addition, various calculations and methods for judging in the human-computer interactive rehabilitation system of the present invention will be described in detail below.

Example 1

Use of the Human-Computer Interactive Rehabilitation System for the Rehabilitation of the Hand Extension and Grip of Patients The embodiment of the present invention is in order to use the human-computer interactive rehabilitation system 1 of the present invention for the rehabilitation of the hand extension and grip of patients with stroke sequelae (hereinafter referred to as the patient). As shown in FIG. 1, the human-computer interactive rehabilitation system 1 of the present invention comprises a visual device 12 which provides a guide screen for the patient to view, a limb sensor 13 which is worn on one of the limbs of the patient to sense the motion of the limb to generate a sensing signal, and an information processing unit 14 which establishes wireless communication with the visual device 12 and the limb sensor 13 (indicated by a dashed line), and the information processing unit 14 further comprises an input signal processing module 141, a rehabilitation operation weight processing module 142, and a content feedback presentation module 143, wherein the wireless communication can be, but not limited to, Bluetooth, and the information processing unit 14 can be, but not limited to, a computer.

Figure 2:
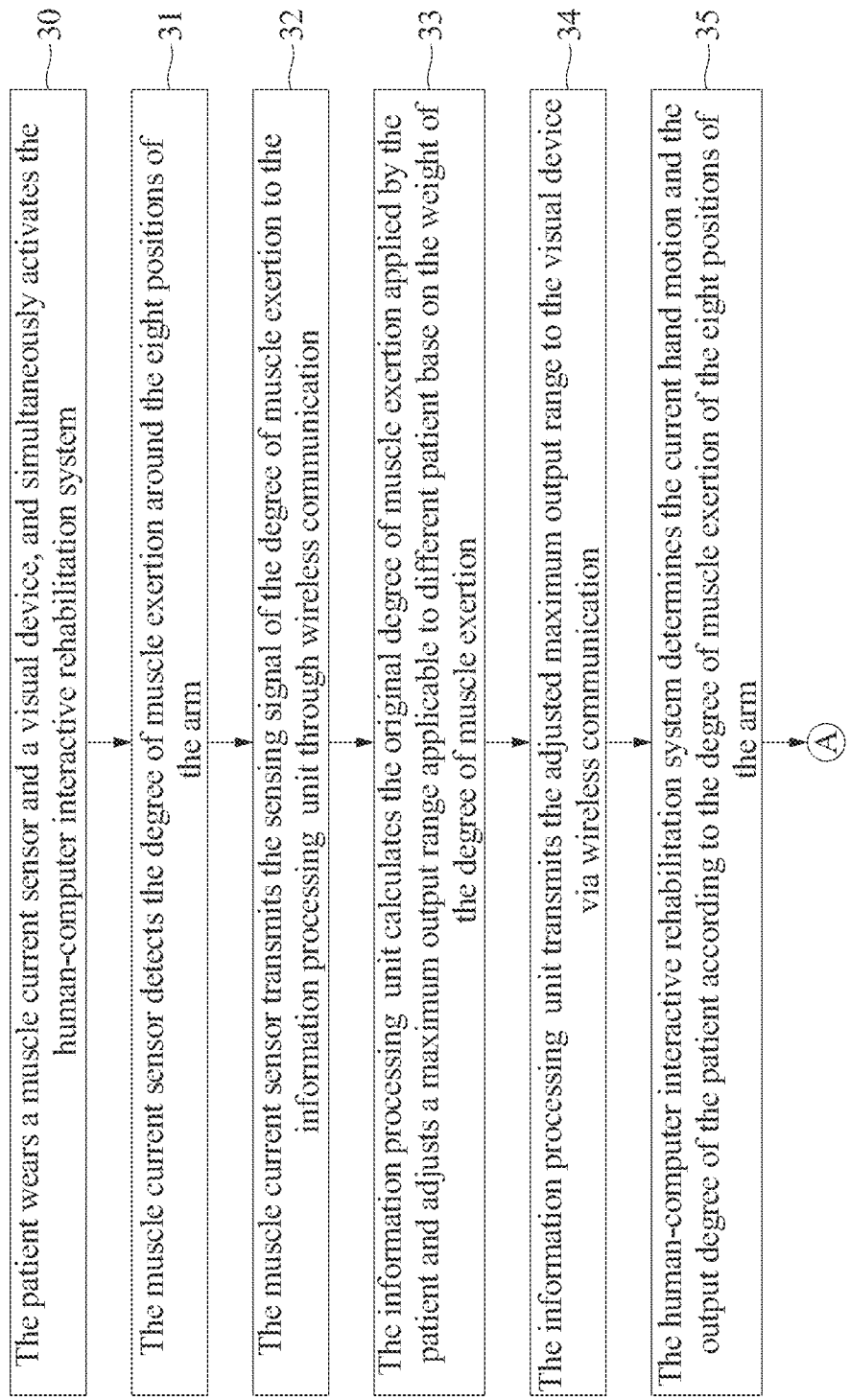
FIG. 2 shows the flow chat of the human-computer interactive rehabilitation system of one embodiment of the present invention for the rehabilitation of the hand extension and grip.
Figure 2:
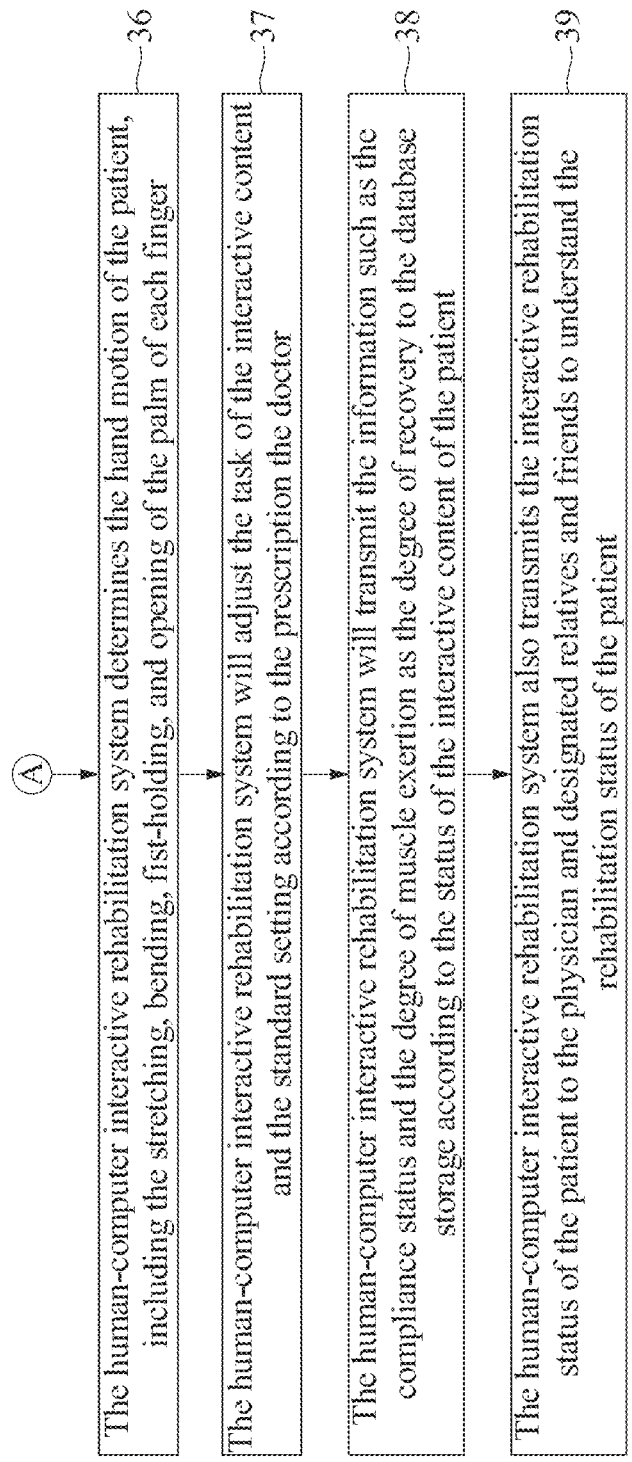

When the patient uses the human-computer interactive rehabilitation system 1 of the present invention to perform hand extension and grip movement, please refer to FIG. 1 and FIG. 2 at the same time. First, the patient is wearing the limb sensor 13, and the visual device 12, and simultaneously opens the human-computer interactive rehabilitation system 1 of the present invention (see FIG. 2, step 30); wherein, the limb sense 13 is a muscle current sensor, and can be, but not limited to, a Myo muscle current sensor, and the muscle current sensor is a ring-shaped wearing device with a plurality of sensing electrode sheets, and the sensing electrode sheets surround the arm which detects the degree of muscle exertion around the arm (see FIG. 2, steps 31 and 35). The visual device 12 is directly worn in front of the eyes of patients or a device capable of presenting a visual image, and can be, but not limited to, intelligent augmented reality glasses, tablets, and smart phones. The human-computer interactive rehabilitation system 1 of the present invention comprises the information processing unit 14 which establishes wireless communication with the visual device 12 and the limb sensor 13 (see FIG. 2, steps 32 and 34), and the information processing unit 14 is further comprises the input signal processing module 141, the rehabilitation operation weight processing module 142, and the content feedback presentation module 143.

The content feedback presentation module 143 in the information processing unit 14 transmits a guide screen to the visual device 12, and the visual device 12 provides the guide screen to the patient for viewing, and if the patient wears the visual device 12 which is directly worn in front of the patient's eyes, the patient can see the guide screen directly in front of the eyes, so that the patient can rotate the head arbitrarily to view the content in different directions without being restricted by the actual environmental space, and can also walk freely. Besides, the patient does not need to go to a specific rehabilitation space or interactive space, and can perform self-rehabilitation exercise exercises at home.

The guide screen can be, but is not limited to, a game animation; and the guide screen leads the patient to perform a rehabilitation motion of hand extension and grip, for example, the guide screen displays milking or scratching balloons, and can guide the patient to do the motion of hand extension and grip, and the limb sensor 13 (e.g., muscle current sensor) worn on the patient will detects the degree of muscle exertion around the eight positions of the arm, and obtains the sensing signal of the eight position, and the sensing signal is transmitted to the rehabilitation operation weight processing module 142 in the information processing unit 14; wherein, the input signal processing module 141 regards the eight muscle current signals received by the muscle current sensor, that is, the sensing signal, as the output status of the muscle positions of the eight positions in the front arm, and reflects the current motion of the hand and the output degree which are used to estimate the motion, bending degree, and output state of the corresponding palm and each finger. For example, the rehabilitation operation weight processing module 142 can calculate the stretching, bending, fisting, and the output of the open palm according to the eight muscle current signals (see FIG. 2, step 36), and further determine the degree of recovery of the patient with sequelae to identify whether the patient actually does the rehabilitation and the specified level of action and output (see FIG. 2, Step 33).

The limb sensor 13 surrounds the arm in a manner like a wristband, and the ring structure is divided into eight orientations to sense eight muscle current signals. Wherein, the back of the hand is oriented in the zero direction, clockwise around a circle, and each of the forty-five degrees interval has a contact electrode to sense the muscle current signal of the azimuth, and each contact electrode presents a different value depending on the different output conditions of the finger and hand movements.

The human-computer interactive rehabilitation system 1 of the present invention has previously recorded that the specific size and waveform of eight muscle current signals of a normal people when they perform specific finger and hand motions, that is, each finger uses different strengths for stretching, bending inward, bending outward, making a fist, and straightening to be the basis for comparison. Wherein, the eight muscle current signals as described in the preceding paragraph represent eight myoelectrically-inductive positions around the forearm, when the patient uses the human-computer interactive rehabilitation system 1 of the present invention and performs the same finger and hand motions, it will observe and record the size and waveform of the eight muscle current signals generated by different finger and hand motions, and compare them with the size and waveform of the eight muscle current signals obtained by the normal people. In general, the size of the muscle current signal in the early stage of rehabilitation is much smaller than the size of muscle current signal from the normal people. Therefore, after a period of rehabilitation, when performing the same finger and hand movements, the size and waveform of the muscle current signals of the patient are significantly increased compared with the initial stage of self-rejuvenation, and the trend of recovery can be judged, and then compared with the size and waveform of the muscle current signal from normal people, if the value is getting closer to the condition of normal people can judge the effect of recovery.

The rehabilitation operation weight processing module 142 simultaneously parameterizes the sensing signal into a numerical range of 0-100 to quantify the output state of the patient. Then, based on the output status of patients, the rehabilitation operation weight processing module 142 calculates the weight according to the patient's current force state, and automatically adjusts a maximum of the range applicable to the patient to calculate a rehabilitation strength suitable for the patient based on the patient's current force state. Since each patient has different initial output or exertion state, the human-computer interactive rehabilitation system 1 of the present invention can automatically adjust to the numerical range of the same applicable interactive operation according to the maximum output range of different patients when they use the human-computer interactive rehabilitation system 1 of the present invention, wherein the multiplication proportional is calculated by multiplying the weight ratio (see FIG. 2, Step 33).

For example: A patient's maximum output range is 0-80, while B patient's maximum output range is 0-60, and the proportional weight of A patient will be 100/80=1.25, and it of B patient will be 100/60=1.67, after calculating the proportional weight, the rehabilitation operation weight processing module 142 records different numerical benchmarks and automatically converts the parameter settings of the human-computer interactive rehabilitation system 1 of the present invention. Wherein, the so-called different numerical benchmarks mean that the maximum output that different patients can make when performing the same rehabilitation exercises will be different; therefore, at the beginning, the maximum output range of each patient will be recorded as the normalization of the response to the game when the patient performs the motions. The benchmark, that is, the maximum output range of patient A is 0-80, the system will convert the input signal from 0-80 to 0-100, and the maximum output range of patient B is 0-60, then the system will convert the input signal from 0-60 to 0-100, and the corresponding reference is stored in the database; wherein, different patients will read different numerical benchmarks. Thus, when different patients interact with the human-computer interactive rehabilitation system 1, they do not need to manually evaluate and adjust the parameter settings in the system in advance, that is, when the sensing signals or the input data are quantized, the numerical normalization processing is performed in advance.

Then, the content feedback presentation module 143 in the information processing unit 14 is used to change the rehabilitation strength suitable for the patient by changing a content of the guide screen to demonstrate the rehabilitation strength suitable for the patient, and the rehabilitation strength is divided into the following two types: one is to increase the number of specified motions completed under a constant output reference value, and the other is to increase the reference value of the output when the number of the same specified motions is complete; wherein, the content feedback presentation module 143 designs different levels of interactive content according to different operation difficulty levels, and different levels of interactive content are different in operation setting. The operation motions are divided into different categories such as continuous operation output, number of interruption operations, specified posture or gesture operation, positioning operation, and thinking judgment operation, and the different categories of grades are operated by representative patients and standardize the difficulty of setting the operation. As described above, the human-computer interactive rehabilitation system 1 of the present invention records the size and waveform of the eight muscle current signals generated by normal people when performing specific motions as a basis for comparison. Thus, when the patient performs the same motions, it is used as a standard for comparing the size of the myoelectric signal of the corresponding positions.

Finally, the content feedback presentation module 143 also uploads the degree of recovery of the patient with limb stroke sequelae to the cloud server 2 for the physician to adjust the prescription (see FIG. 2, steps 37 and 38). Wherein, under the matching of the interactive content and the prescription of the physician, that is, the specified strength of the rehabilitation, the human-computer interactive rehabilitation system 1 of the present invention stores the operation value of each time, for example: the value of each muscle current signal which can be used to observe whether the maximum output range has a gradually increasing trend, whether the length of time to complete the operation is gradually shortening, or the number of observations, the correct rate, and the rate of achievement has gradually increased. By doing so, it can be used to determine the overall degree of recovery of the patient and can be used as a basis for increasing the degree of recovery of the patient.

Therefore, in addition to being able to automatically adjust the rehabilitation content suitable for different patients immediately, the human-computer interactive rehabilitation system 1 of the present invention can also enable the physician to give a new prescription from the remote end through the cloud server 2, thereby increase the difficulty level of the patient operation. In the same time, if the patient cannot immediately reach the rehabilitation strength of the new prescription, the human-computer interactive rehabilitation system 1 of the present invention automatically adjusts the current rehabilitation strength suitable for the patient as described above, and the human-computer interactive rehabilitation system of the present invention will gradually strengthen the rehabilitation strength based on the new prescriptions from the doctors, so that the patient can continue to rebuild the confidence without giving up because of the inability to complete the reconstruction strength. In addition, the human-computer interactive rehabilitation system 1 of the present invention immediately transmit the rehabilitation result to the patient designated caretaker, and then, to provide patient encouragement feedback and strengthen community interaction and link in medical relationship (see FIG. 2, steps 39).

1.1 Guide Screen for Farm Milking

Figure 4A:
FIG. 4A shows the guide screen of the farm milking game in the human-computer interactive rehabilitation system of one embodiment of the present invention.

The embodiment of the present invention is in order to train the rehabilitation motions of the hand extension and grip of the patient, develop an interesting situational game using the human-computer interactive rehabilitation system 1 of the present invention. As shown in FIG. 3, the patient wears the smart augmented reality glasses and the muscle current sensor of the hand; and then, the farm milking game in the human-computer interactive rehabilitation system 1 of the present invention is turned on. Wherein, the smart augmented reality glasses transmit a guide screen of the farm environment to the patient, and a number of cows and a farmer who is milking (see FIG. 4A) appear in the guide screen, and the guide screen will make the patient's perspective of the farmer, and prompt the patient to complete one action of squeezing the milk which promotes the patient to perform the hand extension and grip (see FIG. 3, steps 40 and 41), and the amount of milk in a bucket can be obtained every 40 times of milking (see FIG. 3, step 42).

Figure 4B:
FIG. 4B shows the guide screen of the farm milking game in the human-computer interactive rehabilitation system of one embodiment of the present invention.

Therefore, assuming that the game rehabilitation prescription given by the physician is three buckets of milk per day (see FIG. 3, step 43), the patient has to complete one hundred and twenty times of squeezing milk action (i.e. the hand extension and grip) per day. Wherein, in the guide screen of the farm milking game, the white area of the cow will drop a little with each milk (see FIG. 4B), just as the milk of the cow is slowly squeezed out to increase the fun of the game (see FIG. 3, step 46).

In this situational game, the patients wear the smart augmented reality glasses, so that they can see the guide screen directly on the glasses, and the patient can rotate the head arbitrarily to view the content in different directions without being restricted by the actual environmental space, and can also walk freely. Besides, the patient does not need to go to a specific rehabilitation space or interactive space, and can perform self-rehabilitation exercise exercises at home (see FIG. 3, steps 44 and 45). In addition, the intelligent augmented reality glasses worn on the patient can still see the surrounding environment to reduce the sense of dizziness and fear caused by the completely immersive viewing mode (see FIG. 3, step 47).

1.2 Guide Screen for Squeezing Balloons

Figure 5:
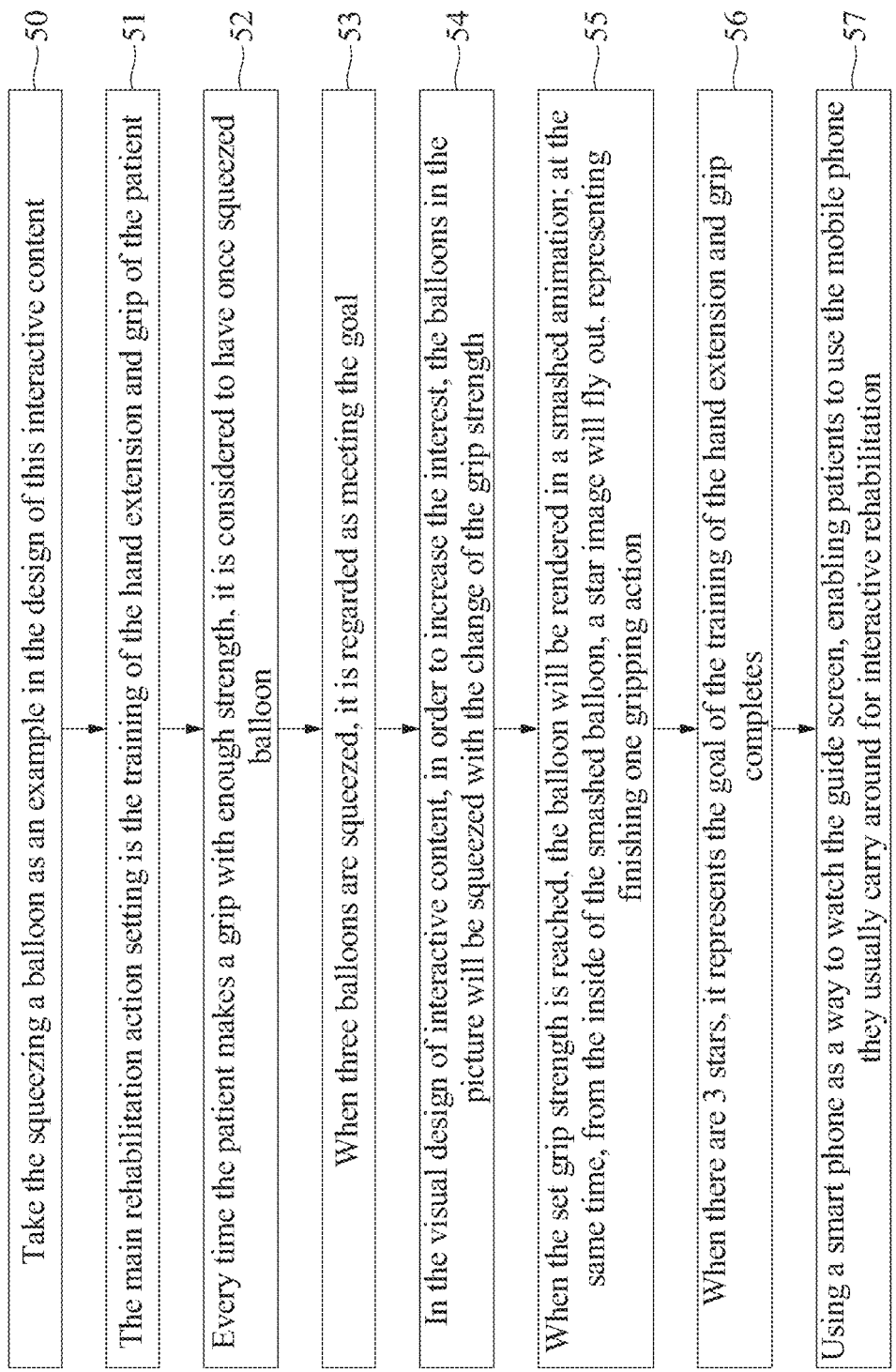
FIG. 5 shows the flow chat of the squeezing balloons game in the human-computer interactive rehabilitation system of one embodiment of the present invention.
Figure 6A:
FIG. 6A shows the guide screen of the squeezing balloons game in the human-computer interactive rehabilitation system of one embodiment of the present invention.
Figure 6B:
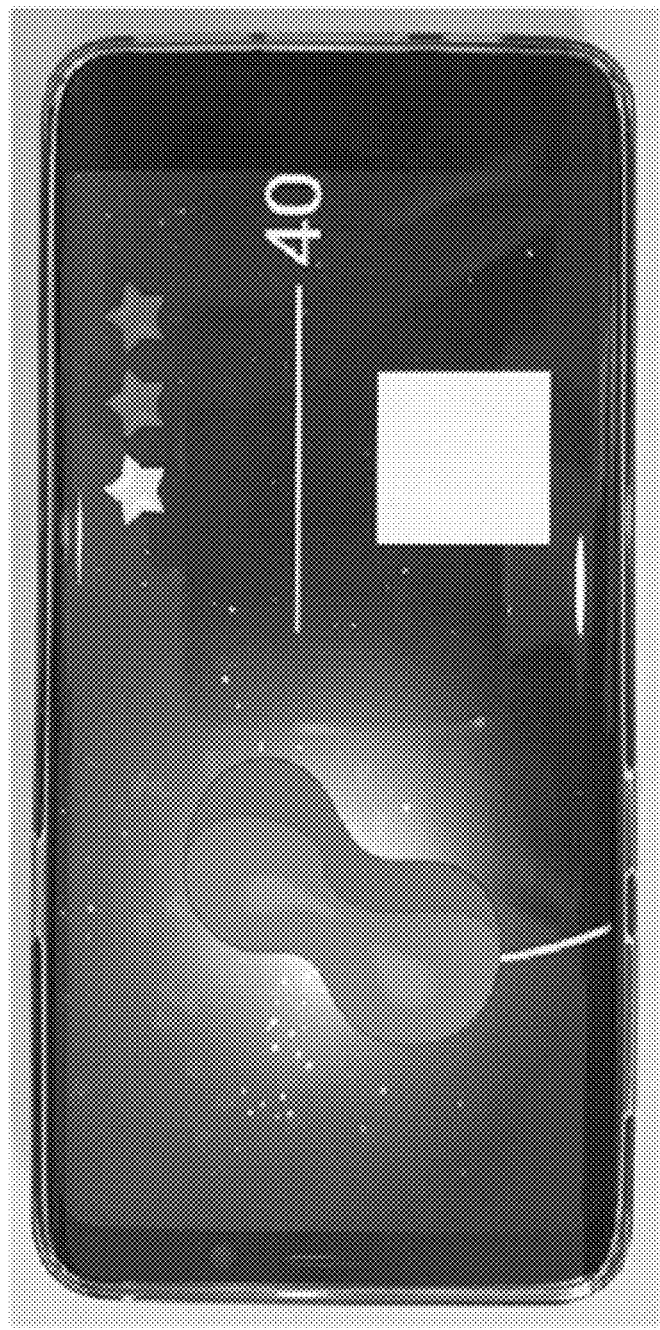
FIG. 6B shows the guide screen of the squeezing balloons game in the human-computer interactive rehabilitation system of one embodiment of the present invention.
Figure 6C:
FIG. 6C shows the guide screen of the squeezing balloons game in the human-computer interactive rehabilitation system of one embodiment of the present invention.

The embodiment of the present invention is in order to train the rehabilitation motions of the hand extension and grip of the patient, develop an interesting situational game using the human-computer interactive rehabilitation system 1 of the present invention; wherein, this situational game is a simple type of the aforementioned farm milking game. As shown in FIG. 5, first, the patient only wears the muscle current sensor of the hand, and is equipped with a device capable of presenting a guide screen, such as a smart phone, loaded with the human-computer interactive rehabilitation system 1 of the present invention, and then the squeezing balloons game in the human-computer interactive rehabilitation system 1 of the present invention is turned on. Wherein, the guide screen of the situational game will be directly displayed on the screen of the device (see FIG. 6A), and the patient can repeatedly perform the action of the hand extension and grip by looking at the guide screen of the game content on the screen of the device (see FIG. 5, steps 50 and 51) to perform a rehabilitation exercise. This situational game will transmit the image of the balloon and the amount of force applied to the hand. Every time the patient makes a grip with enough strength, the balloon will be squeezed (see FIGS. 6B and 6C), which is considered to have once squeezed balloon (see FIG. 5, steps 52 and 55).

Therefore, assuming that the game prescription given by the physician is required to complete the squeezing of 30 balloons per day, the patient needs to complete 30 times of the hand extension and grip actions every day (see FIG. 5, Step 53 and 56). In addition, in order to increase the interest, the balloons in the picture will be squeezed with the change of the grip strength (see FIG. 5, step 54; and FIG. 6B), and when the balloon is squeezed, from the inside of the smashed balloon, a star image will fly out, representing finishing one gripping action (see FIG. 5, step 55; and FIG. 6C). This situational game provides rejuvenation through devices which can present visual images, such as smart phones, and muscle current sensors in a simple environment (see FIG. 5, step 57).

Example 2

Use of the Human-Computer Interactive Rehabilitation System for the Rehabilitation of the Spatial Neglect Syndrome The embodiment of the present invention is in order to use the human-computer interactive rehabilitation system 1 of the present invention for the rehabilitation of patients with stroke sequelae of the visual disorder (hereinafter referred to as the patient), especially in patients with the spatial neglect syndrome. Patients with the spatial neglect syndrome may have neglected or invisible symptoms for the spatial visual field on one side therefore strengthening the concentration practice of patients on the side of the spatial vision ignore is the focus of rehabilitation.

Figure 7:
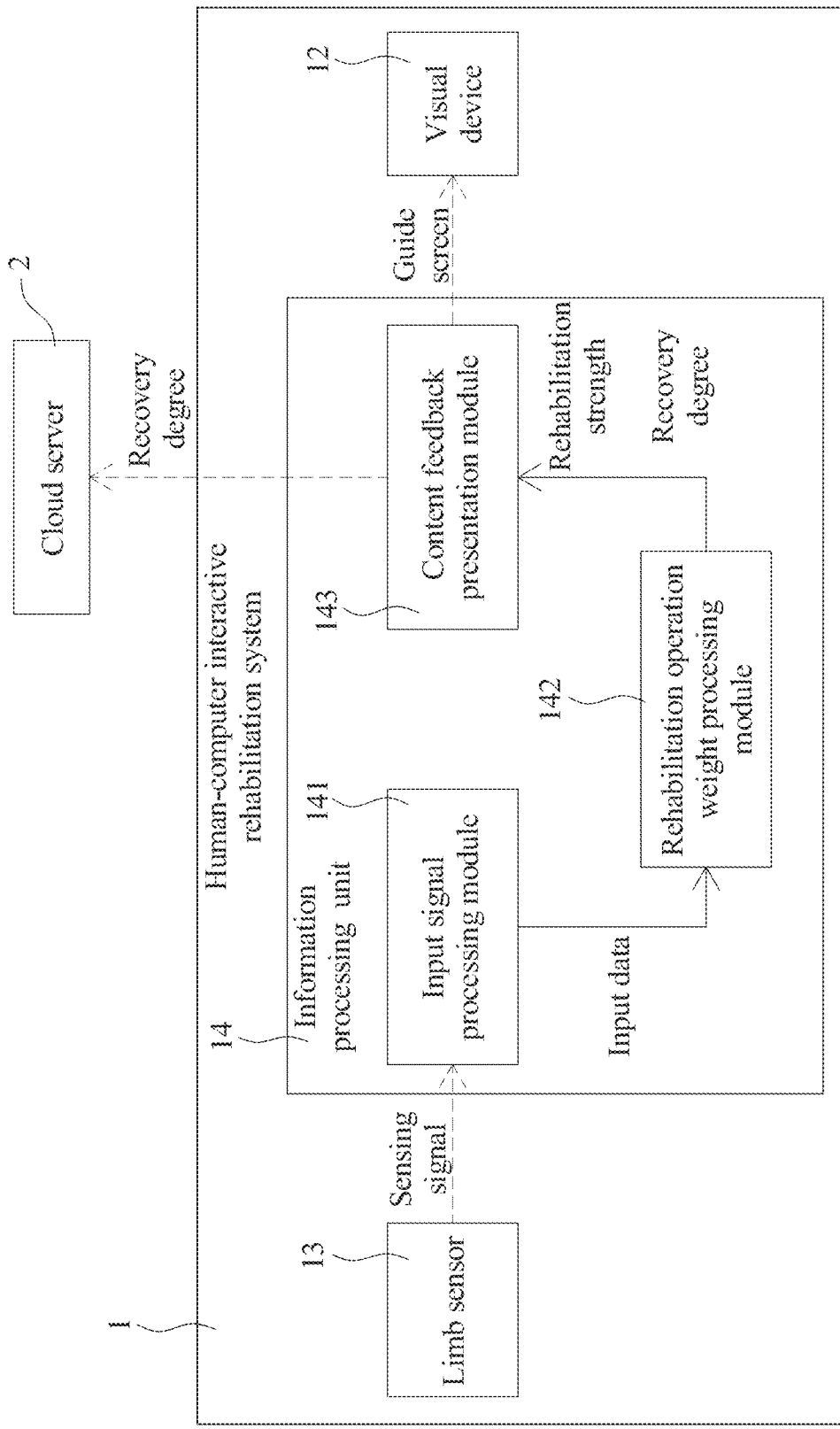
FIG. 7 shows the architecture diagram of the human-computer interactive rehabilitation system of one embodiment of the present invention for the rehabilitation of the patients with the spatial neglect syndrome.

As shown in FIG. 7, the human-computer interactive rehabilitation system 1 of the present invention comprises a visual device 12 which provides a guide screen for the patient to view and an information processing unit 14 which establishes wireless communication with the visual device 12 (indicated by a dashed line), and the information processing unit 14 further comprises a human machine interface 144, a rehabilitation operation weight processing module 142, and a content feedback presentation module 143.

Figure 8:
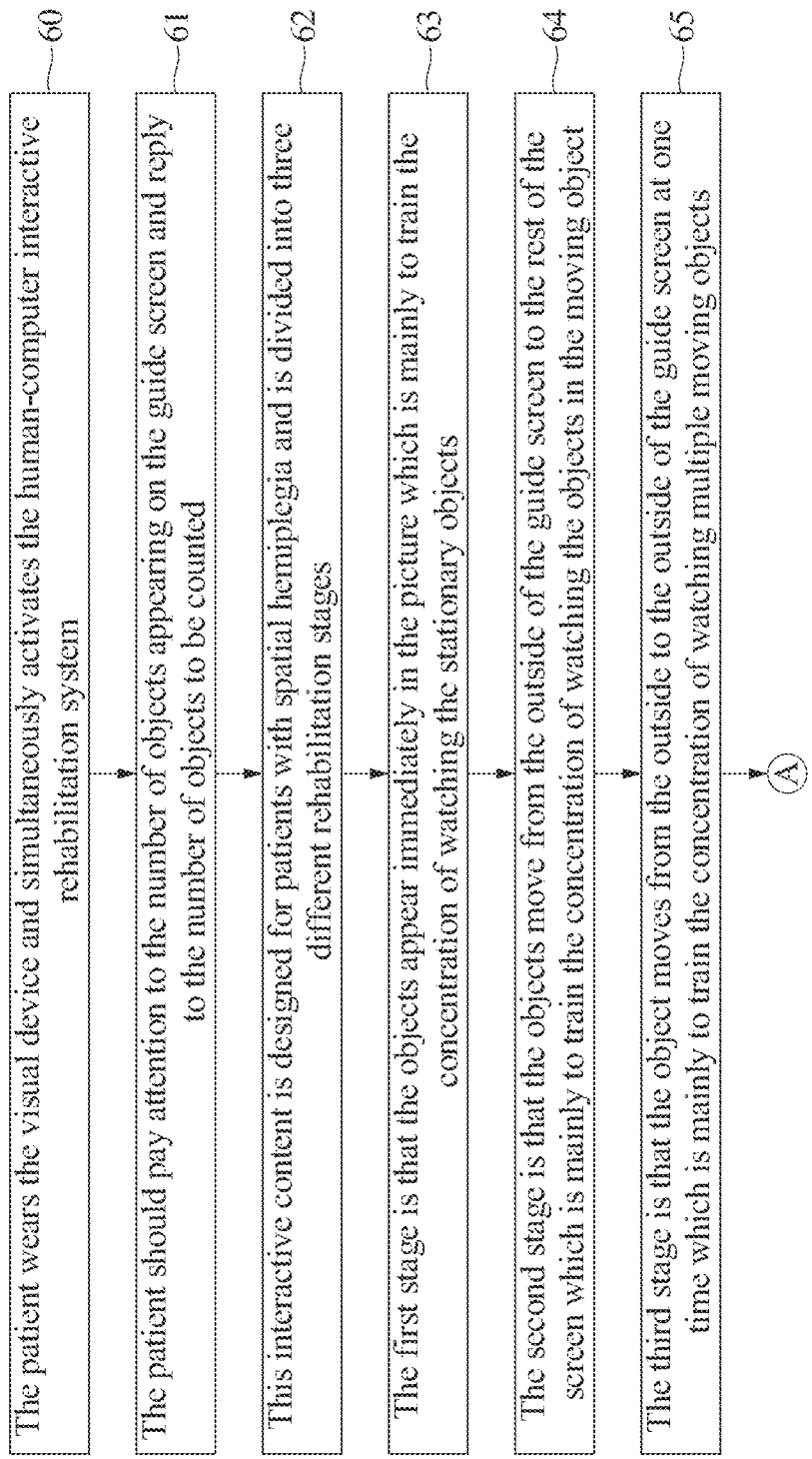
FIG. 8 shows the flow chart of the human-computer interactive rehabilitation system of one embodiment of the present invention for the rehabilitation of the patients with the spatial neglect syndrome.
Figure 8:
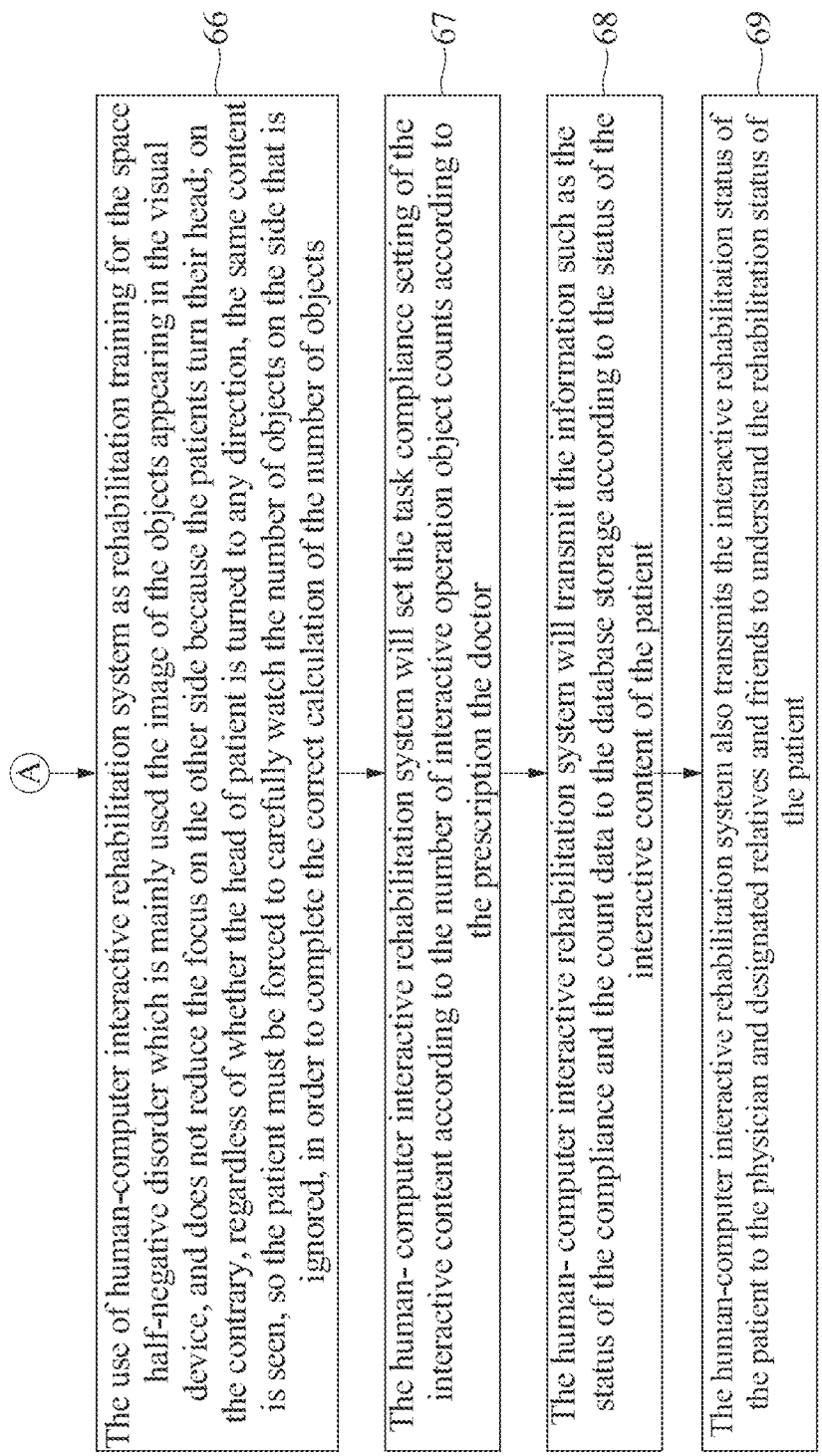

When the patient uses the human-computer interactive rehabilitation system 1 of the present invention to rehabilitate the spatial neglect syndrome, please refer to FIG. 7 and FIG. 8 at the same time. First, the patient is wearing the visual device 12 and simultaneously opens the human-computer interactive rehabilitation system 1 of the present invention (see FIG. 8, steps 60 and 62); wherein, the visual device 12 is directly worn in front of the eyes of patients, and can be, but not limited to, intelligent augmented reality glasses. The human-computer interactive rehabilitation system 1 of the present invention comprises the information processing unit 14 which establishes wireless communication with the visual device 12, and the information processing unit 14 is further comprises the human machine interface 144, the rehabilitation operation weight processing module 142, and the content feedback presentation module 143.

The content feedback presentation module 143 in the information processing unit 14 transmits a guide screen to the visual device 12, and the visual device 12 provides the guide screen to the patient for viewing, and if the patient wears the visual device 12 which is directly worn in front of the patient's eyes, the patient can see the guide screen directly in front of the eyes, so that the patient can rotate the head arbitrarily to view the content in different directions without being restricted by the actual environmental space, and can also walk freely. Besides, the patient does not need to go to a specific rehabilitation space or interactive space, and can perform self-rehabilitation exercise exercises at home. Wherein, The guide screen can be, but is not limited to, a game animation.

For patients with the spatial neglect syndrome, it is mainly necessary to strengthen the visual concentration of patients therefore when the human-computer interactive rehabilitation system 1 of the present invention is used for the rehabilitation of the spatial neglect syndrome; it is designed with the visual focus of the patient's need to bet. Wherein, the guide screen directs the patient to count the plurality of objects, and the guide screen is divided into the following three different counting stages: the first stage is that the objects appear immediately in the picture which is mainly to train the concentration of watching the stationary objects (see FIG. 8, steps 63), the second stage is that the objects move from the outside of the guide screen to the rest of the screen which is mainly to train the concentration of watching the objects in the moving object (see FIG. 8, steps 64), and the third stage is that the object moves from the outside to the outside of the guide screen at one time which is mainly to train the concentration of watching multiple moving objects (see FIG. 8, steps 65). In the stage of the three different counting modes, the patient inputs the number of the plurality of objects to be counted (see FIG. 8, step 61), and the quantity input by the patient is an input data 132, and the input data 132 is transmitted to the rehabilitation operation weight processing module 142 in the information processing unit 14; wherein, the rehabilitation operation weight processing module 142 analyzes the input data 132 to determine the degree of recovery of the stroke sequelae, that is, automatically determine the visual concentration of the patients.

The human-computer interactive rehabilitation system 1 of the present invention mainly uses the number of objects to be counted in the guide screen to derive the degree of recovery of the patient, that is, as a basis for the patient to improve visual concentration. This kind of design is mainly for the problem that the patients with the spatial neglect syndrome cannot focus on the half of the things visually. Therefore, in the process of counting, the phenomenon that the patient counts incorrectly can be used as a basis for judging the degree of recovery of the patient. If the correct rate of the counting is increased, it can be judged that the visual concentration of the patient is relatively improved.

The human-computer interactive rehabilitation system 1 of the present invention is used as rehabilitation training for the spatial neglect syndrome, mainly by using the image of the object appearing in the visual device which does not follow the movement of the patient, instead, regardless of the turning head to any direction, patients see the same content, forcing the patient to carefully concentrate on the number of objects on the visual side that is ignored, in order to complete the correct number of objects calculation (see FIG. 8, step 66). Wherein, in the dynamic movement training of the second stage and the third stage, it is because that the dynamic environment is mostly in the real environment. Especially when walking on the road, patients need to pay attention to the car, other pedestrians or items around, so as not to hit them because the spatial neglect syndrome.

The rehabilitation operation weight processing module 142 also automatically estimates rehabilitation strength suitable for the patient, since each patient has different symptoms at the initial stage, and result in different patients have different visual attention. The human-computer interactive rehabilitation system 1 of the present invention can automatically determine different visual attention concentration of different patients, and automatically adjust to the same interactive operation range applicable to the human-computer interactive rehabilitation system 1 of the present invention. Wherein, the multiplication proportional is calculated by multiplying the weight ratio, and the visual concentration of the normal people is taken as the reference value, that is, 100%. When the different patients are in the initial rehabilitation, the correct rate of counting will be different. The human-computer interactive rehabilitation system 1 of the present invention calculates the correct rate by the input data 132 from the patient, and then calculates the multiplication proportional by the correct rate, and automatically determines the standardized counting level and difficulty level applicable to the patient, that is, a small counting range (1-5 objects), a medium counting range (1-10 objects), and a high counting range (1-15 objects), and the appropriate counting stages applicable to the patient.

The human-computer interactive rehabilitation system 1 of the present invention allows the patient to perform ten counting exercises in three different levels of each counting stage, and then calculates each correct rate; wherein, the three different levels in the three stages, that is, the result of the nine counts, the count correctness rates are all set to 100% in normal people. Therefore, in the early phase of rehabilitation, the patient is first asked for operating three different levels of the three stages, and the correct rate of the nine counting results is recorded as a criterion for judging the level and difficulty level when subsequent using the human-computer interactive rehabilitation system 1 of the present invention. Wherein, when the correct rate reaches 80% or more, it will enter the difficulty of the next exercise, and the order of difficulty is a small counting range of the first stage, a medium counting range of the first stage, a high counting range of the first stage, a small counting range of the second stage, a medium counting range of the second stage, a high counting range of the second stage, a small counting range of the third stage, a medium counting range of the third stage, and a high counting range of the third stage.

Furthermore, since the image of the plurality of objects to be counted appears on the smart augmented reality glasses, the plurality of objects to be counted are always fixedly present on the glasses, unlike when viewing a solid object, the patient can view the field of view in different directions by turning the head, which makes it difficult to practice the neglected side of the visual side. Through the human-computer interactive rehabilitation system 1 of the present invention, the plurality of objects to be counted are projected on the smart augmented reality glasses, and even if the patient turns the head, the plurality of objects to be counted will rotate synchronously, so that the patient has to focus on the side of the spatial field of view to count the objects to be counted on that side, and then can count to the correct amount (see FIG. 8, steps 66 and 67).

Then, the content feedback presentation module 143 in the information processing unit 14 is used to change the rehabilitation strength suitable for the patient by changing a content of the guide screen to demonstrate the rehabilitation strength suitable for the patient; wherein, the content feedback presentation module 143 designs different levels of interactive content according to different operation difficulty levels. In different operation difficulty levels of interactive content in the guide screen, the patient can see that the setting of the plurality of objects to be counted and the setting of the counting mode are different; wherein, the guide screen is changed to match the rehabilitation strength of each patient, and the rehabilitation strength is divided into the following two types: one is to increase the number of the plurality of objects to be counted without changing the stage, and the other is to count similar number of the plurality of objects in the next stage, that is, the first stage enters the second stage, or the second stage enters the third stage.

Each stage will randomly appear several different numbers of objects to be counted according to the counting range of different levels, that is, the aforementioned the small to high counting range, and let the patient reply to the plurality of objects to be counted. Each stage will perform about 10 times, and when the correct rate of patient response increases, it will proceed to the next stage. Thus, when different patients interact with the human-computer interactive rehabilitation system 1, they do not need to manually evaluate and adjust the parameter settings in the system in advance, that is, when the human-computer interactive rehabilitation system 1 of the present invention is just started, the process of numerical normalization is performed in advance, that is, the guide screen is adjusted to suit the visual concentration applicable to each different patient (see FIG. 8, step 68).

Finally, the content feedback presentation module 143 also uploads the degree of recovery of the patient with stroke sequelae of the visual disorder to the cloud server 2 for the physician to adjust the prescription (see FIG. 8, steps 68). Wherein, under the matching of the interactive content and the prescription of the physician, that is, the specified strength of the rehabilitation, the human-computer interactive rehabilitation system 1 of the present invention stores the operation value of each time, for example: whether the visual field of patients has a tendency to gradually expand, whether the length of time to complete the operation is gradually shortened, and whether the correct rate, and the achievement rate are gradually increasing. By doing so, it can be used to determine the overall degree of recovery of the patient and can be used as a basis for increasing the degree of recovery of the patient.

Therefore, in addition to being able to automatically adjust the rehabilitation content suitable for different patients immediately, the human-computer interactive rehabilitation system 1 of the present invention can also enable the physician to give a new prescription from the remote end through the cloud server 2, thereby increase the difficulty level of the patient operation. In the same time, if the patient cannot immediately reach the rehabilitation strength of the new prescription, the human-computer interactive rehabilitation system 1 of the present invention automatically adjusts the current rehabilitation strength suitable for the patient as described above, and the human-computer interactive rehabilitation system of the present invention will gradually strengthen the rehabilitation strength based on the new prescriptions from the doctors, so that the patient can continue to rebuild the confidence without giving up because of the inability to complete the reconstruction strength. In addition, the human-computer interactive rehabilitation system 1 of the present invention immediately transmit the rehabilitation result to the patient designated caretaker, and then, to provide patient encouragement feedback and strengthen community interaction and link in medical relationship (see FIG. 8, steps 69).

2.1 Guide Screen for Catching Fish in a Pond

Figure 9A:
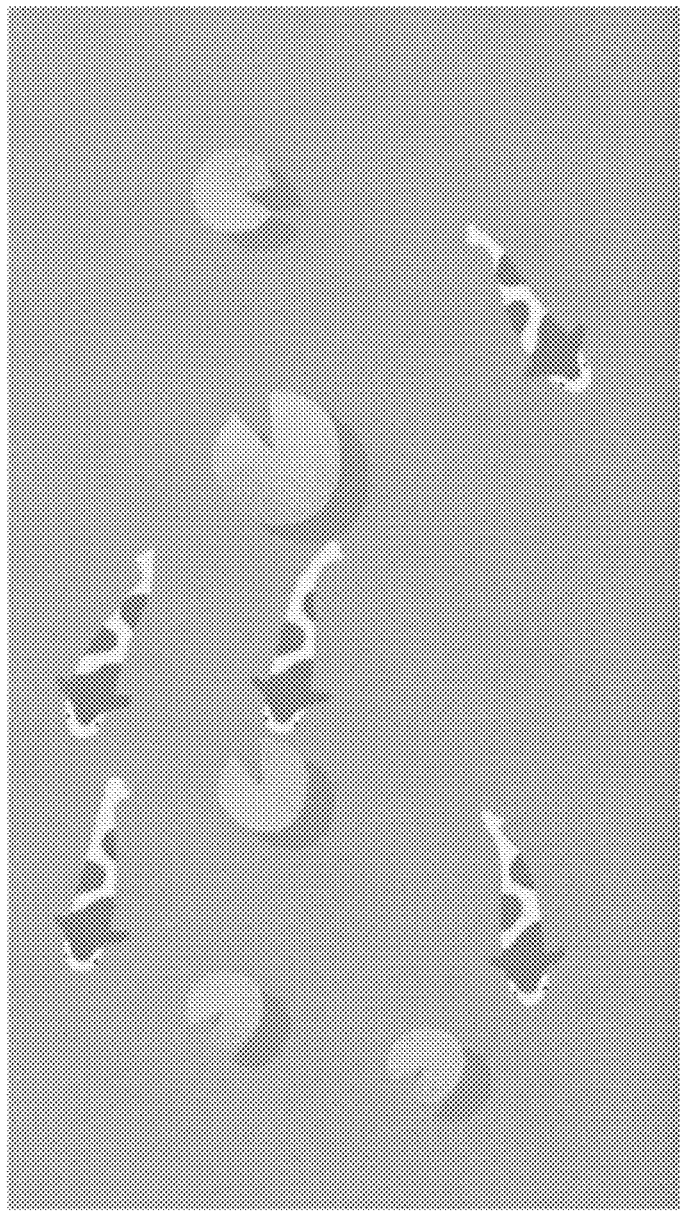
FIG. 9A shows the guide screen of the catching fish in a pond game in the human-computer interactive rehabilitation system of one embodiment of the present invention.
Figure 9B:
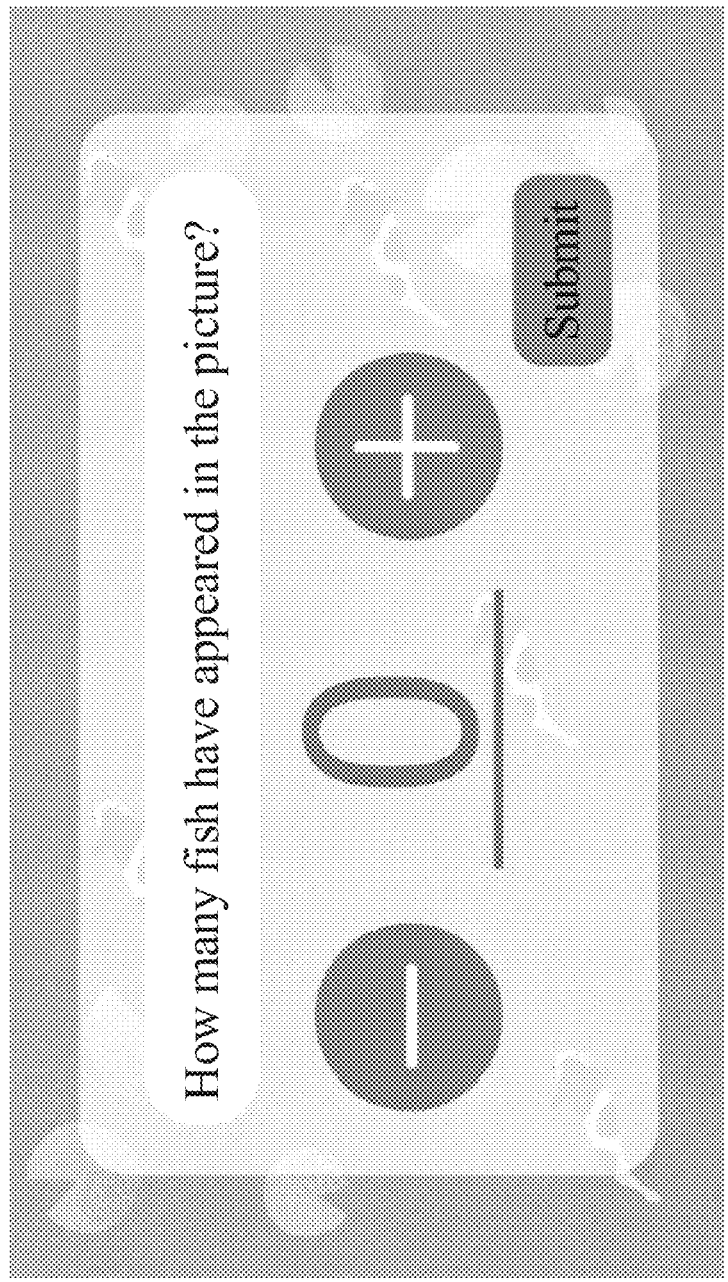
FIG. 9B shows the guide screen of the catching fish in a pond game in the human-computer interactive rehabilitation system of one embodiment of the present invention.
Figure 9C:
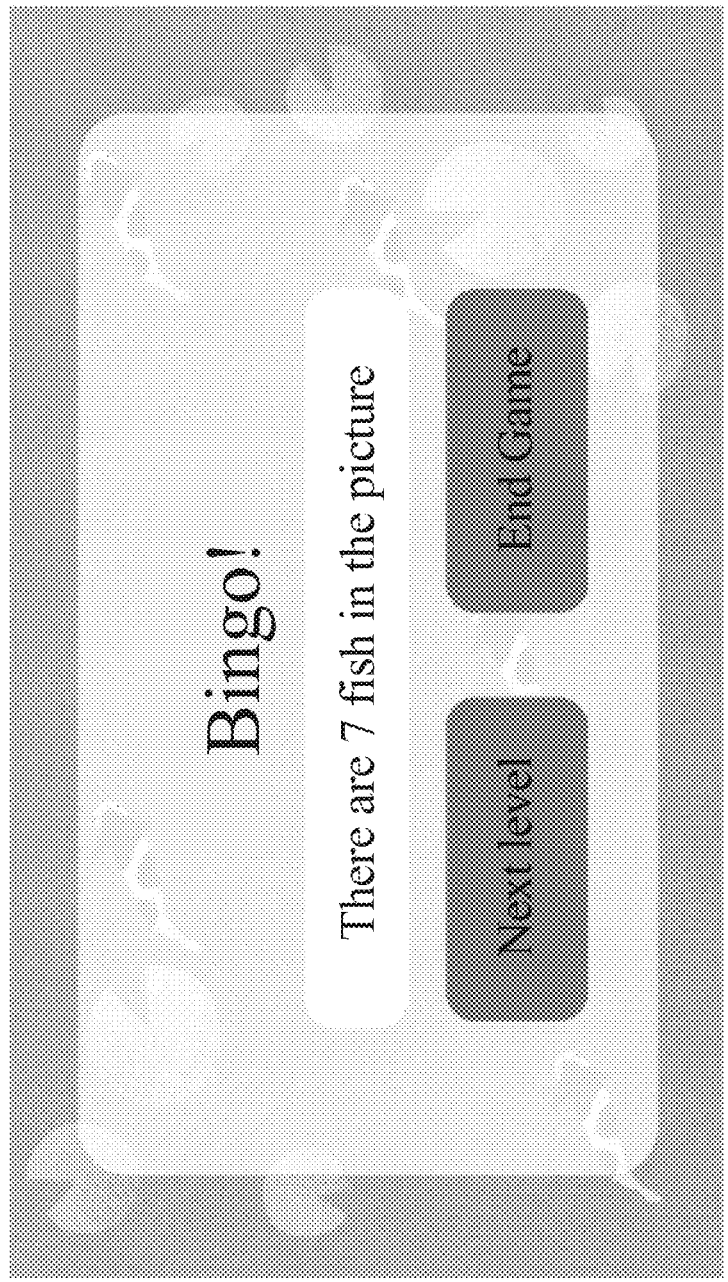
FIG. 9C shows the guide screen of the catching fish in a pond game in the human-computer interactive rehabilitation system of one embodiment of the present invention.
Figure 9D:
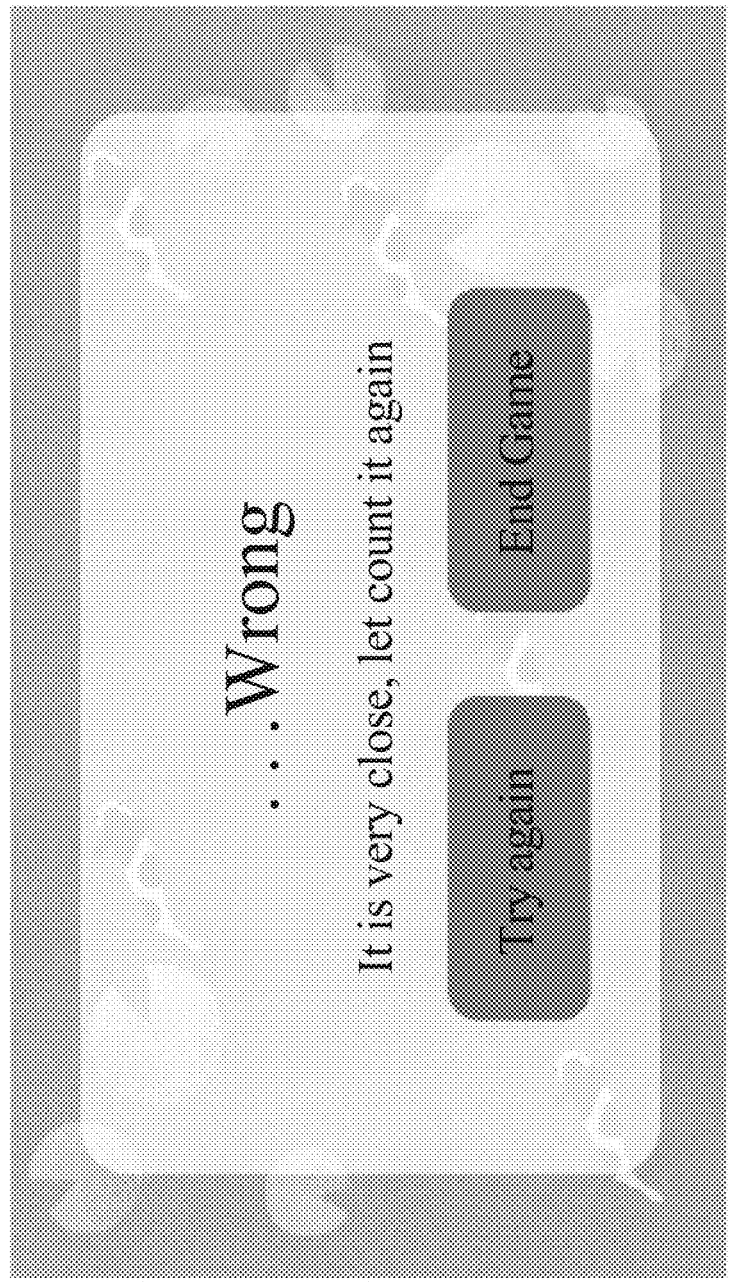
FIG. 9D shows the guide screen of the catching fish in a pond game in the human-computer interactive rehabilitation system of one embodiment of the present invention.
Figure 10:
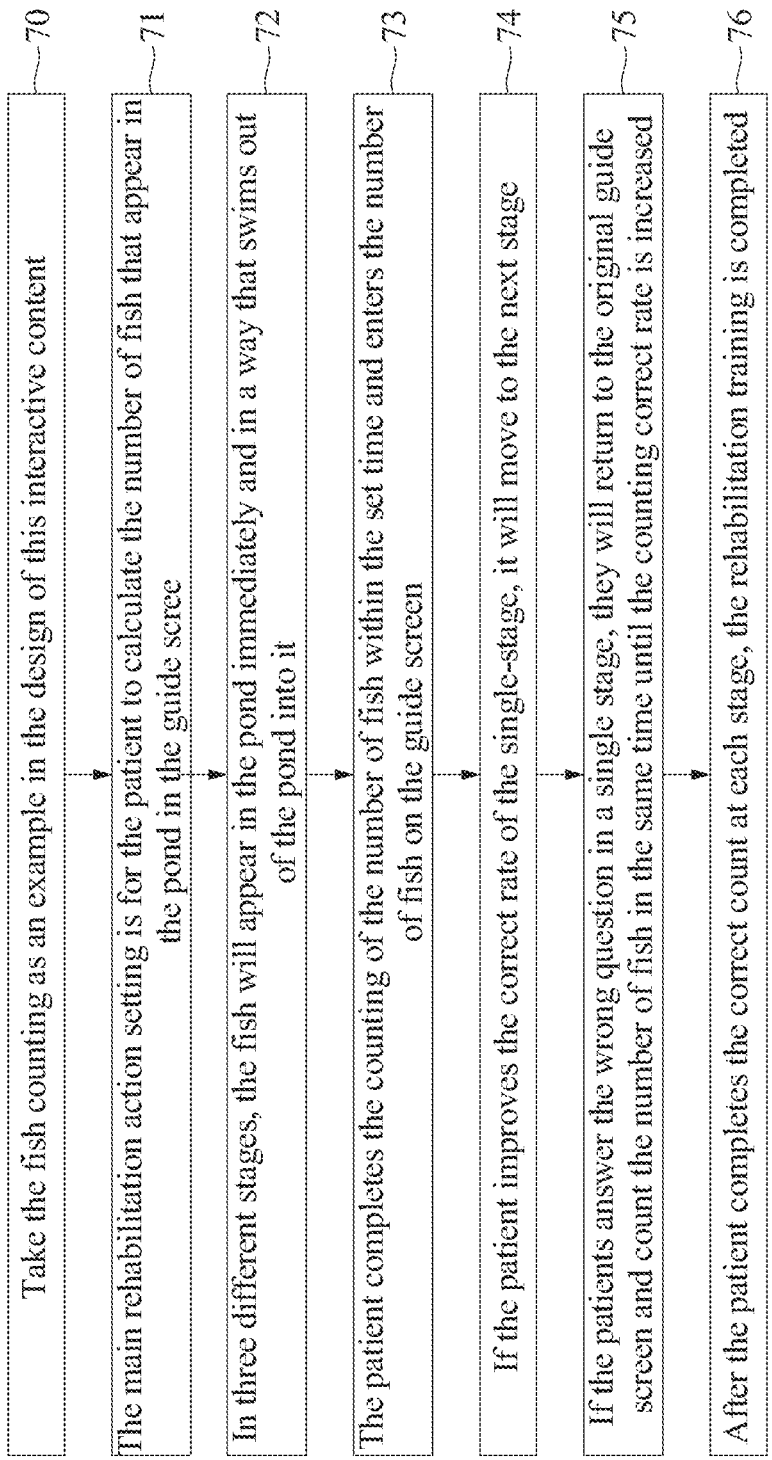
FIG. 10 shows the flow chart of the catching fish in a pond game in the human-computer interactive rehabilitation system of one embodiment of the present invention.

The embodiment of the present invention is in order to train the rehabilitation of patients with stroke sequelae of the visual disorder, especially in patients with the spatial neglect syndrome, develop an interesting situational game using the human-computer interactive rehabilitation system 1 of the present invention. As shown in FIG. 10, the patient wears the smart augmented reality glasses at first, and then the catching fish in a pond game in the human-computer interactive rehabilitation system 1 of the present invention is turned on (see FIG. 10, steps 70). The intelligent augmented reality glasses transmit a guide screen of a plurality of fish swimming in a pond to the patient in a fixed position in the pond, and are distributed at various positions of the guide screen (see FIG. 9A). Then, the patient needs to watch the guide screen and calculate how much fish in the guide screen (see FIG. 9B), and if the answer is correct, it is considered complete one counting (see FIG. 10, Step 71; and FIG. 9C). The rehabilitation is divided into the above three stages. Each successful answer to the question of one stage will automatically enter the next stage. If the answer is not correct, the practice of the same stage will continue until the count is correct (See FIG. 10, steps 72-75; and FIG. 9D).

Therefore, assuming that the game rehabilitation prescription given by the physician is to correctly calculate the number of fish ten times per day, the patient has to correctly answer the number of fish in ten questions and then can be considered as completing a daily rehabilitation (see FIG. 10, step 76).

In the interactive game content, the way the fish appears in the guide screen is also the important point of practicing concentration. For example, the fish appears in the guide screen once, or swims one by one in the guide screen, or swims in and out of in the guide screen. The manner of presentation can be automatically determined by the human-computer interactive rehabilitation system 1 of the present invention or by the physician according to the symptoms of the patient to arrange which kind of visual concentration practice has to do.

In summary, the human-computer interactive rehabilitation system 1 of the present invention can automatically adjust to the same applies to different patients according to the maximum output range of different patients in the practice of the hand extension and grip rehabilitation of patients with stroke sequelae; and in the rehabilitation practice of the patient with stroke sequelae of the visual disorder, the field vision of patients can be automatically determined by the data input 132 by the patient to infer the affected side of the specific spatial field of view of different patients, and the input signal processing module 143 automatically estimates a rehabilitation strength suitable for the patient. In this way, when using the human-computer interactive rehabilitation system of the present invention, different patients do not need to manually evaluate and adjust the parameter settings in the system in advance, that is, when the sensing signals or the input data are quantized, the numerical normalization processing is performed in advance. The human-computer interactive rehabilitation system 1 of the present invention designs different levels of interactive content according to different operation difficulty levels, and different levels of interactive content are different in operation setting, thereby improving rehabilitation efficiency after stroke.

The human-computer interactive rehabilitation system 1 of the present invention can track the rehabilitation status and intervene at any time through the data platform, establish a cloud community feedback encouragement mechanism on the platform, and immediately transmit the rehabilitation result to the patient designated caretaker, and then, to provide patient encouragement feedback and strengthen community interaction and link in medical relationship. The human-computer interactive rehabilitation system 1 of the present invention also stores the operation value of each time, so that in addition to being able to automatically adjust the rehabilitation content suitable for different patients immediately, the physician can also give a new prescription from the remote end through the cloud server 2. In addition, if the patient cannot immediately reach the rehabilitation strength of the new prescription, the human-computer interactive rehabilitation system of the present invention automatically adjusts the current rehabilitation strength suitable for the patient as described above, and the human-computer interactive rehabilitation system of the present invention will gradually strengthen the rehabilitation strength based on the new prescriptions from the doctors, so that the patient can continue to rebuild the confidence without giving up because of the inability to complete the reconstruction strength.

Therefore, the human-computer interactive rehabilitation system of the present invention can be used for the reconstruction of stroke sequelae, and can enter the home reconstruction through legal retailing and provide qualified people, families, or unit rents. The human-computer interactive rehabilitation system of the present invention can also be used in conjunction with local rehabilitation hospitals and clinics in conjunction with relevant acute post-care policies and comprehensive elderly care plans, and is applied to rehabilitation hospitals for rehabilitation prescription and treatment, and can also cooperate with community rehabilitation, home health care and technical care to provide patients in need.

What is claimed is:

1. A rehabilitation system for stroke sequelae, comprising:
a visual device for providing a guide screen to a patient;
a limb sensor worn on a limb of the patient to sense a motion of the limb to generate a sensing signal; and
an information processing unit which establishes wireless communication with the visual device and the limb sensor, and comprises an input signal processing module, a rehabilitation operation weight processing module, and a content feedback presentation module;
wherein, the content feedback presentation module transmits the guidance screen to the visual device, and the input signal processing module receives the sensing signal from the limb sensor and transmits the sensing signal to the rehabilitation operation weight processing module, and then the rehabilitation operation weight processing module estimates a current hand motion of the patient according to the sensing signal, and derives various actions of the patient to determine a recovery degree of the stroke sequelae of the limb of the patient, and the rehabilitation operation weight processing module simultaneously parameterizes the sensing signal into a range of values as a current force state of the patient, and automatically adjusts a maximum of the range applicable to the patient to calculate a rehabilitation strength suitable for the patient based on the current force state of the patient, and the content feedback presentation module changes a content of the guide screen to demonstrate the rehabilitation strength suitable for the patient;
wherein, the content feedback presentation module uploads the recovery degree of the stroke sequelae of the patient to a cloud server;
wherein, the limb sensor is a muscle current sensor.

2. The rehabilitation system according to claim 1, wherein the stroke sequelae is about a hand movement disorder.

3. The rehabilitation system according to claim 1, wherein the guide screen is to direct the patient to perform a hand grip training.

4. The rehabilitation system according to claim 3, wherein the guiding screen guides the patient to perform the hand grip training according to the sensing signal and the rehabilitation strength suitable for the patient.

5. The rehabilitation system according to claim 1, wherein the recovery degree of the stroke sequelae of the patient is related to autonomous movement and arm muscle control.

6. The rehabilitation system according to claim 1, wherein the limb sensor surrounds the limb with a ring structure; wherein the ring structure is divided into eight orientations to sense eight muscle current signals; wherein each orientation has a contact electrode to sense a muscle current signal.

* * * * *